United States Patent [19]

Daniel

[11] 4,429,136
[45] Jan. 31, 1984

[54] MANUFACTURE OF MALEIC ANHYDRIDE
[75] Inventor: Chelliah Daniel, Columbus, Ohio
[73] Assignee: Ashland Oil, Inc., Ashland, Ky.
[21] Appl. No.: 443,254
[22] Filed: Nov. 22, 1982
[51] Int. Cl.$^3$ ............................................ C07D 307/60
[52] U.S. Cl. ...................................... 549/258; 502/211
[58] Field of Search ........................................... 549/258

[56] References Cited
U.S. PATENT DOCUMENTS
4,093,635  6/1978  Bremer et al. ....................... 549/258

*Primary Examiner*—Henry R. Jiles
*Assistant Examiner*—Bernard Dentz
*Attorney, Agent, or Firm*—John F. Jones

[57] ABSTRACT

A process for the oxidation of n-butane, n-butenes, 1,3-butadiene and mixtures thereof to maleic anhydride in the vapor phase over a catalyst having the empirical formula $Cu_aP_bMn_cMo_dO_x$ wherein a is 0.001 to 1.0, b is 0.01 to 2.0, c is 0.001 to 2.0, d is 1.0 to 20.0, and x is a number which satisfies the unshared valences of the other elements in the formula is described.

4 Claims, No Drawings

MANUFACTURE OF MALEIC ANHYDRIDE

This invention relates to the preparation of maleic anhydride by the catalytic oxidation of n-butane, n-butenes, 1,3-butadiene, or combinations thereof and particularly pertains to an improved catalyst for the oxidation process.

Maleic anhydride is a well-known chemical intermediate for many purposes including the manufacture of polyester resin. Although catalysts for the preparation of maleic anhydride by the oxidation of n-butane, n-butenes, and 1,3-butadiene are known, the yields of the desired maleic anhydride are often low and subject to improvement.

Prior art catalysts proposed for the oxidation of n-butane to maleic anhydride have generally been based on vanadium and phosphorous. U.S. Pat. No. 3,293,268 describes such a catalyst. In order to improve vanadium-phosphorous catalysts, many proposals have been offered to incorporate other additives, stabilizers or promoters to the basic vanadium-phosphorous catalyst. In this regard, reference is made to U.S. Pat. Nos. 4,219,484; 4,244,878; 4,244,879; 4,251,390; 4,288,372; 4,293,443; 4,304,723; British Pat. No. 1,591,307, and Japanese Pat. No. SHO 54[1979]-21323.

Thus, the preponderance of the catalysts described in the prior art useful for the oxidation of n-butane to maleic anhydride contain vanadium as an essential component.

It is accordingly an object of this invention to provide a catalyst which is free of vanadium and is highly useful for the production of maleic anhydride from n-butane.

It is also an object of this invention to provide a process for the oxidation of n-butane, n-butenes, 1,3-butadiene or mixtures thereof to maleic anhydride.

These and other objectives are accomplished in accordance with the present invention by use of a catalyst system composed of the combined oxides of copper, phosphorous, manganese, and molybdenum. The catalysts useful in this invention can be further defined as those conforming to the empirical formula $Cu_aP_bMn_cMo_dO_x$ wherein a is 0.001 to 1.0, b is 0.01 to 2.0, c is 0.001 to 2.0, d is 1.0 to 20.0, and x is a number which satisfies the unshared positive valences of the other elements present in the formula.

The catalysts of this invention can be prepared in any convenient manner by procedures known to those skilled in the art of catalyst manufacture. It will be understood that the invention is not limited to catalysts prepared by any particular method of manufacture.

It is preferred that the catalyst be calcined in air or in an inert atmosphere at a temperature in the range of 200° C. to 600° C. before it is used in the oxidative reaction of this invention.

The catalyst can be used in the process of this invention in the form of pellets, discs, wafers, balls, or any other convenient shape which can be used in the reactors employed in the oxidation reaction of this invention. The catalyst can be deposited on a carrier if desired.

Although fixed bed reactors are usually used in the oxidation process to produce maleic anhydride, fluidized bed reactors can also be used in which case the catalyst should be used in a particle-size range which is known to be useful in a fluidized bed oxidation process.

The oxidation of n-butane to maleic anhydride, for instance, may be accomplished by contacting the n-butane and oxygen with the catalyst described herein. Air is a satisfactory source of oxygen although mixtures of oxygen and inert gases such as nitrogen may also be employed.

The oxidation process of this invention is carried out at a temperature of from 360° C. to 500° C. and preferably from 380° C. to 450° C. The concentration of n-butane or other hydrocarbon in the feed will be from 0.1 to 2.0% with air being present in from 98.0% to 99.9% (by volume). The oxidation reaction of this invention may be carried out at atmospheric, sub-atmospheric or super-atmospheric pressure, but substantially atmospheric pressure is preferred. As mentioned previously, the process of this invention can be carried out in any apparatus suitable for effective vapor-phase oxidation reactions, but preferably a fixed bed, tubular reactor is used.

Maleic anhydride and lesser amounts of acrylic acid and acetic acid which are prepared from n-butane by the process of this invention can be recovered by any number of means which are well known to those skilled in the art. For instance, the reaction effluent can be condensed or absorbed in suitable media with subsequent separation and purification of the desired product components.

The following examples will further illustrate the invention.

EXAMPLE 1

A slurry was prepared from 200 g. of ammonium dimolybdate, 11.5 g. of manganese chloride, 12.5 g. of cupric nitrate and 36.0 g. of 85% phosphoric acid. The slurry was stirred and dried by evaporation on a hot plate for 16 hours and the resulting solid was further dried in an air oven at 150° C. for 8 hours. The product was then calcined at 400° C. in air for 6 hours. Analysis of the catalyst thus prepared showed that it had the empirical formula $Cu_{0.5}P_{3.0}Mn_{0.58}Mo_{10.0}O_x$.

EXAMPLE 2

The catalyst of Example 1 was ground to 12–20 mesh and 45.0 cc of this material was packed in a 13″ tube reactor of stainless steel having a ¾ inch diameter. The catalyst bed was supported with a pre- and post-quartz chip packing. The feed to the reactor was made up of air and n-butane. The following table gives the experimental conditions used and the results obtained in a series of runs.

TABLE

| Run | Temp., °C. | GHSV* | Mole % n-butane In Feed | Percent Conversion of n-butane | Selectivity MA** | AA*** | HAC**** |
|---|---|---|---|---|---|---|---|
| 1 | 389 | 1261 | 1.57 | 49.4 | 19.8 | 10.8 | 5.2 |
| 2 | 401 | 2524 | 1.6 | 18.4 | 44.1 | 20.6 | 6.8 |
| 3 | 420 | 2530 | 1.55 | 19.35 | 43.85 | 21.21 | 6.5 |

TABLE-continued

| Run | Temp., °C. | GHSV* | Mole % n-butane In Feed | Percent Conversion of n-butane | Selectivity | | |
|---|---|---|---|---|---|---|---|
| | | | | | MA** | AA*** | HAC**** |
| 4 | 420 | 2528 | 1.55 | 19.87 | 44.01 | 21.57 | 6.7 |

*Gas hourly space velocity
**Maleic anhydride
***Acrylic acid
****Acetic acid

I claim:

1. The process for production of maleic anhydride comprising the oxidation of n-butane, n-butenes, 1,3-butadiene or mixtures thereof with molecular oxygen in the vapor phase at a temperature in the range of from about 360° C. to 500° C. in the presence of a catalyst having the empirical formula $Cu_aP_bMn_cMo_dO_x$ wherein a is 0.001 to 1.0, b is 0.01 to 2.0, c is 0.001 to 2.0, d is 1.0 to 20.0, and x is a number which satisfies the unshared positive valences of the other elements in the formula.

2. The process of claim 1 wherein n-butane is oxidized to maleic anhydride.

3. The process of claim 2 wherein the molecular oxygen is in the form of air.

4. The process of claim 2 wherein the catalyst has the empirical formula $Cu_{0.5}P_{3.0}Mn_{0.58}Mo_{10.0}O_x$.

* * * * *